United States Patent [19]

Kanost et al.

[11] Patent Number: 5,196,304
[45] Date of Patent: Mar. 23, 1993

[54] SERINE PROTEINASE INHIBITOR GENE FROM THE INSECT *MANDUCA SEXTA*

[75] Inventors: Michael R. Kanost; Michael A. Wells, both of Tucson, Ariz.; Sarvamangala V. Prasad, Houston, Tex.

[73] Assignee: Arizona Technology Development Corporation, Tucson, Ariz.

[21] Appl. No.: 464,310

[22] Filed: Jan. 12, 1990

[51] Int. Cl.$^5$ .......................... C07H 21/04; C12Q 1/68
[52] U.S. Cl. ....................... 435/6; 536/23.2; 536/23.5; 935/9
[58] Field of Search ................... 536/27; 435/6; 935/9

[56] References Cited

PUBLICATIONS

Kanost, et al., "Primary Structure of a Member of the Serpin Superfamily of Proteinase Inhibitors from an Insect, *Manduca sexta*" The Journal of Biological Chemistry, vol. 264, No. 2, Jan. 15, 1989 pp. 965–972.
Boswell, et al., "Genetic Engineering and The Serpins" BioEssays 8, 83–87, 1988.
Bao, et al., "Molecular Evolution of Serpins: Homologous Structure of the Human alpha1-Antichymotrypsin and alpha1-Antitryspin Genes" Biochemistry, 1987, 26, 7755–7759.
Suzuki, et al., "Characterization of a cDNA for Human Protein C Inhibitor", Journal of Biological Chemistry vol. 262, No. 2 Jan. 15, 1987, pp. 611–616.
Holmes, et al., "Primary Structure of Human alpha2-Antiplasmin, a Serine Protease Inhibitor (Serpin)" Journal of Biological Chemistry, vol. 262, No. 4, Feb. 5, 1987, pp. 1659–1664.
Hill, et al, "Accelerated Evolution in the Reactive Center Regions of Serine Protease Inhibitors", nature, vol. 326 Mar. 5, 1987 pp. 96–99.
Sommer, et al., "cDNA Sequence Coding for a Rat Glia-Derived Nexin and Its Homology to Members of the Serpin Superfamily" Biochemitry, 1987, 26, 6407–6410.
Pickup, et al., "Hemorrhage in Lesions Caused by Cowpox Virus is Induced by a Viral Protein that is Related to Plasma Protein Inhibitors of Serine Proteases", Proc. Nat. Acad. Sci. U.S.A. vol. 83, pp. 7698–7702 Oct. 1986, Biochemistry.
Ny, et al., "Cloning and Sequence of a cDNA Coding for the Human Beta-Migrating Endothelial-Cell-Type Plasminogen Activator Inhibitor" Proc. Natl. Acad. Sci. U.S.A., vol. 83, pp. 6776–6780, Sep. 1986 Biochemistry.
Carrell, et al., "Serpins: the Superfamily of Plasma Serine Proteinase Inhibitors", Protein Inhibitors, 1986, Chapter 12 pp. 403–420.
Pannekoek, et al., "Endothelial Plasminogen Activator Inhibotor (PAI): a New Member of the Serpin Gene Family" pp. 2539–2544, Jun. 30, 1986.
Carrell, et al., "Alpha1-Antitrypsin and the Serpins: Variation and Countervariation", TIBS, Jan. 1985, pp. 20–24.
Chandra, et al., "Sequence Homology Between Human Alpha1-Anti-Chymotryspin, Alpha1-Antitrypsin and Antithromobin III" Biochemistry, vol. 22, No. 22, Oct. 25, 1983, pp. 5055–5060.
Chandra, et al., "Isolation and Sequence Characterization of a cDNA Clone of Human Antithrombin III" Proc. Natl. Acad. Sci. U.S.A. vol. 80, pp. 1845–1848, Apr. 1983, Biochemistry.
Prochownik, et al., "Isolation of a cDNA Clone for Human Antithrombin III", Journal of Biological Chemistry, vol. 258 No. 13, Jul. 10, 1983, pp. 8389–8394.
Travis, et al., "Human Plasma Proteinase Inhibitors", Amn. Rev. Biochem. 1983, 52:655–709.
Carrell, et al., "Structure and Variation of Human Alpha1-Antitrypsin" Nature, vol. 298, No. 22, Jul. 1982, pp. 329–334.

(List continued on next page.)

*Primary Examiner*—John W. Rollins
*Assistant Examiner*—Gary L. Kunz

[57] ABSTRACT

Disclosed is a cDNA clone isolated from a fat body cDNA library from the tobacco hornworm *Manduca sexta*, and the deduced amino acid sequence of the serine proteinase inhibitor encoded by the cDNA.

4 Claims, 3 Drawing Sheets

PUBLICATIONS

Beatty, et al., "Kinetics of Association of Serine Proteinases with Native and Oxidized alpha-I-Proteinase Inhibitor and alpha-1 Antichymotrypsin", Journal of Biological Chemistry, vol. 255, No. 9 May 10, 1980, pp. 3931–3934.

Kurachi, et al., "Cloning and Sequence of cDNA Coding for Alphal-Antitrypsin" Proc. Natl. Acad. Sci U.S.A., vol. 78, No. 11 pp. 6826–6830, Nov. 1981, Biochemistry.

Hill, et al., "Plasma Protease Inhibitors in Mouse and Man: Divergence within the Reactive Center Regions", Nature, vol. 311, Sep. 13, 1984, pp. 175–177.

1 2 3 4 5

```
   1 GAGTGGGACGTTCGGCACAGCAACATGAAGATTATTATGTGTATATTTGGCCTTGCGGCC
 -16                           M  K  I  I  M  C  I  F  G  L  A  A

61 TTGGCCATGGCTGGCGAGACGGATCTGCAGAAGATTTTACGAGAAAGCAACGACCAATTT
  -4  L  A  M  A  G  E  T  D  L  Q  K  I  L  R  E  S  N  D  Q  F
              -1 +1

121 ACAGCCCAGATGTTTTCTGAAGTGGTAAAAGCGAACCCTGGTCAAAACGTCGTGTTGTCT
  17  T  A  Q  M  F  S  E  V  V  K  A  N  P  G  Q  N  V  V  L  S

181 GCATTCTCCGTCCTGCCACCATTGGGCCAACTGGCTTTGGCTTCCGTAGGTGAATCACAC
  37  A  F  S  V  L  P  P  L  G  Q  L  A  L  A  S  V  G  E  S  H

241 GACGAACTGCTAAGAGCTTTGGCTTTACCCAACGACAATGTGACGAAAGATGTATTTGCG
  57  D  E  L  L  R  A  L  A  L  P  N  D  N  V  T  K  D  V  F  A

301 GATCTAAACCGTGGTGTGCGAGCTGTCAAAGGAGTCGATCTGAAGATGGCCAGTAAAATT
  77  D  L  N  R  G  V  R  A  V  K  G  V  D  L  K  M  A  S  K  I

361 TATGTAGCAAAAGGTCTTGAACTTAATGATGACTTCGCGGCAGTATCAAGAGACGTTTTC
  97  Y  V  A  K  G  L  E  L  N  D  D  F  A  A  V  S  R  D  V  F

421 GGTTCTGAAGTCCAAAATGTAGACTTTGTAAAGAGCGTTGAAGCAGCCGGCGCGATTAAC
 117  G  S  E  V  Q  N  V  D  F  V  K  S  V  E  A  A  G  A  I  N

481 AAATGGGTTGAAGATCAAACCAACAATCGCATCAAAAATTTAGTCGACCCAGATGCGTTG
 137  K  W  V  E  D  Q  T  N  N  R  I  K  N  L  V  D  P  D  A  L

541 GACGAAACAACACGCTCCGTTCTCGTCAATGCTATATACTTCAAGGGTAGCTGGAAAGAC
 157  D  E  T  T  R  S  V  L  V  N  A  I  Y  F  K  G  S  W  K  D

601 AAGTTTGTCAAGGAAAGAACAATGGACAGAGACTTCCATGTTTCCAAAGACAAAACAATT
 177  K  F  V  K  E  R  T  M  D  R  D  F  H  V  S  K  D  K  T  I

661 AAAGTGCCTACTATGATCGGTAAGAAGGATGTCCGTTACGCTGATGTTCCTGAACTTGAT
 197  K  V  P  T  M  I  G  K  K  D  V  R  Y  A  D  V  P  E  L  D

721 GCTAAGATGATTGAAATGTCATATGAGGGTGACCAAGCATCTATGATTATTATATTACCC
 217  A  K  M  I  E  M  S  Y  E  G  D  Q  A  S  M  I  I  I  L  P

781 AACCAAGTAGACGGAATCACAGCACTGGAACAAAAACTGAAGGATCCTAAAGCTCTTTCA
 237  N  Q  V  D  G  I  T  A  L  E  Q  K  L  K  D  P  K  A  L  S

841 AGAGCTGAGGAGCGTTTGTACAACACTGAAGTTGAAATTTACCTTCCAAAATTCAAAATT
 257  R  A  E  E  R  L  Y  N  T  E  V  E  I  T  L  P  K  F  K  I

901 GAAACAACTACCGATCTGAAAGAAGTTCTTAGTAACATGAACATCAAAAAATTGTTCACT
 277  E  T  T  T  D  L  K  E  V  L  S  N  M  N  I  K  K  L  F  T

961 CCAGGAGCAGCTAGACTAGAGAATCTTTTAAAAACAAAGGAATCTTTATATGTAGATGCG
 297  P  G  A  A  R  L  E  N  L  L  K  T  K  E  S  L  T  V  D  A

1021 GCTATACAAAAAGCTTTTATCGAAGTCAACGAAGAAGGTGCAGAGGCTGCGGCTGCTAAC
 317  A  I  Q  K  A  F  I  E  V  N  E  E  G  A  E  A  A  A  A  N

1081 GCTTTCGGTATCGTACCGGCGAGTTTGATACTATATCCAGAAGTTCATATCGATCGACCT
 337  A  F  G  I  V  P  A  S  L  I  L  T  P  E  V  H  I  D  R  P

1141 TTCTACTTTGAACTTAAGATTGATGGTATCCCCATGTTCAACGGCAAAGTTATCGAACCT
 357  F  Y  F  E  L  K  I  D  G  I  P  M  F  N  G  K  V  I  E  P

1201 TAATGCTTTCTTTATTATAGAATCATATTCTTCGTATGAACCTGTCGTACCCGTCTTTGA
      ---

1261 CATAGATAAACCTTTTTACTTCAACATAAGAGCTAATGGCCAGTCTTTGTTCAACGGGCT

1321 ATGTTTCCAACCATAAAACGATATATTGTTATCATTAAGAAACATTAACAATAACGTCCG

1381 GTTGGAATGTAATCAAATCACTTTTATACAAACAATAAACATTTTCT
```

FIG 3

SERINE PROTEINASE INHIBITOR GENE FROM THE INSECT *MANDUCA SEXTA*

BACKGROUND OF THE INVENTION

The present invention relates generally to the primary structure of a member of the serpin superfamily of proteinase inhibitors from the insect *Manduca sexta*. More specifically, the present invention relates to a cDNA clone isolated from a fat body cDNA library from a lepidopteran insect, the tobacco hornworm *M. sexta*, and the deduced amino acid sequence of the serpin.

The serpins are a superfamily of serine proteinase inhibitors. Human plasma contains serpins which are similar in amino acid sequence and mechanism of inhibition, but differ in their specificity toward proteolytic enzymes. The serpin superfamily includes proteins of about $M_r=50,000-100,000$, which function in regulation of blood clotting (antithrombin-III, heparin cofactor-II, antiplasmin, protein C inhibitor), complement activation (C1 inhibitor), and proteinases released from neutrophils ($\alpha_1$-antitrypsin,$\alpha_1$-antichymotrypsin). The serpin superfamily also includes endothelial plasminogen activator inhibitor, glia-derived nexin, mouse contrapsin, ovalbumin, angiotensinogen, barley endosperm protein Z, and cowpox virus 38-kDa protein. Comparisons of the amino acid sequences of these individual serphins reveal an sequence identity of about 20-30%, with the greatest sequence conservation appearing at the COOH-terminal half of the proteins.

In contrast, much less is known about proteinase inhibitors from invertebrates. Most of the proteinase inhibitors isolated from invertebrates have been in the low $M_r$ range of about 5,000–15,000. A $M_r=155,000$ proteinase inhibitor has been isolated from crayfish plasma and an $\alpha_2$-macroglobulin-like proteinase inhibitor has been isolated from hemolymph of the American Lobster.

The only proteinase inhibitors isolated from invertebrates which are similar in size and characteristics to the serpins are a trypsin inhibitor ($M_r=42,000$) and a chymotrypsin inhibitor ($M_r=43,000$) which have been isolated from the hemolymph of the silkworm Bombyx mori. While some bioreactive similarities with the serpins exist, sequencing of the first 18 NH$_2$-terminal amino acids of these two silkworm proteinase inhibitors have revealed no similarity to the human serpins. The complete sequence data, which would show whether these silkworm proteins are evolutionarily related to the serpins, is not yet available.

SUMMARY OF THE INVENTION

The present invention presents the cDNA cloning and deduced amino acid sequence of a serpin from the insect *Manduca sexta*. The invention provides, for the first time, a serine proteinase inhibitor cloned from an insect. The gene expressing the serpin is expressed in the fat body and the protein, an active serine proteinase inhibitor is present in the hemolymph. The cDNA has an open reading frame which codes for a 392-residue polypeptide of $M_r=43,500$, with a hydrophobic NH$_2$-terminal sequence which appears to be a signal peptide. Alignment of the deduced amino acid sequence with eleven known members of the serpin superfamily reveals that the *M. sexta* protein exhibits a 25–30% homology with most members of the superfamily. The alignment was used to construct an evolutionary tree of the serpin sequences. The evolutionary tree indicates that the progenitor of the *M. sexta* serpin and the human serpins most closely related to it diverged from other serpin genes prior to the divergence of the vertebrates and invertebrates. The *M. sexta* serpin is believed to inhibit elastase due to the presence of alanine at the P$_1$ position of its reactive center and is, therefore, classified as an alaserpin. A glycoprotein of $M_r=47,000$, isolated from the hemolymph of *M. sexta* larvae has an identical NH$_2$-terminal sequence to that deducted from the alaserpin cDNA clone. This glycoprotein has been shown to inhibit porcine pancreatic elastase and bovine chymotrypsin. The cDNA clone may be modified by site directed mutagenesis to optimize specificity of the inhibitor for various serine proteases.

BRIEF DESCRIPTION OF THE DRAWINGS

FIG. 3 is the cDNA and deduced amino acid sequences of *M. sexta* alaserpin.

DETAILED DESCRIPTION OF THE PREFERRED EMBODIMENT

Figure 1:
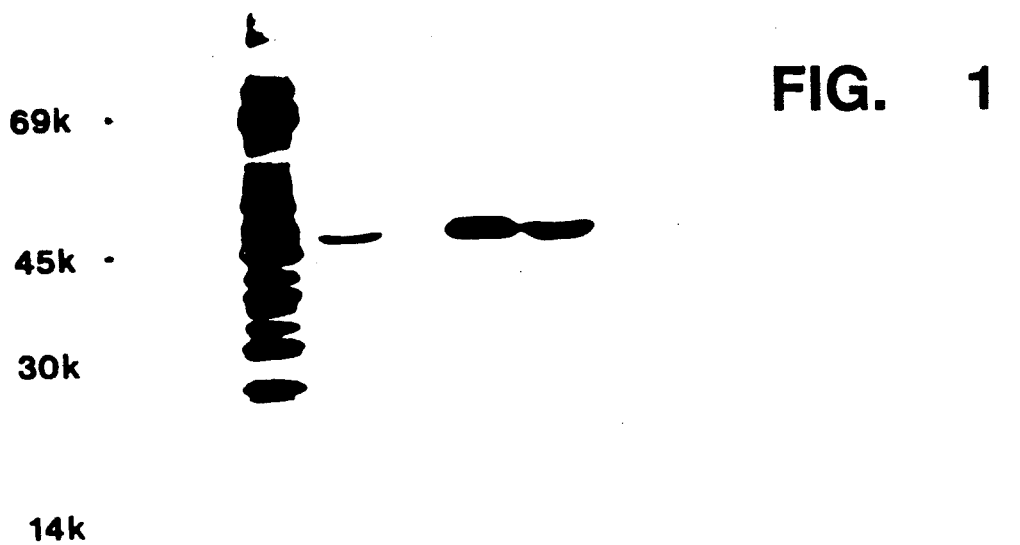
FIG. 1 is a SDS-polyacrylamide gel electrophoresis pattern of RNA translation products and immunoprecipitated proteins. Lane 1 represents protein standards; lane 2 represents translation products from polyadenylated RNA from fat body of day 2 fifth instar *M. sexta* larvae; lane 3 represents translation products precipitated by antiserum to apolipophorin-II; lane 4 represents translation products of RNA selected by hybridization with alaserpin cDNA; and lane 5 represents translation products of hybridselected RNA immunoprecipitated.

According to the present invention, cDNA and deducted amino acid sequences encoding all or part of a polypeptide sequence of a serine proteinase inhibitor from the insect *Manduca sexta* has been isolated, purified and characterized. The serpin is expressed in the fat body and the protein is secreted into the hemolymph.

The serine proteinase inhibitor cDNA was isolated from the fat body cDNA library. Total RNA from the fat body of *M. sexta* larvae was isolated and polyadenylated RNA was selected by passing the total RNA through an oligo(dT)-cellulose column. The polyadenylated RNA was used to prepare cDNA and a cDNA library was constructed in λgt11 and screened with antiserum to *M. sexta* apolipophorin-II. Analysis of 12,000 recombinant plaques yielded two positive clones which were purified to homogeneity. The two positive clones were digested to reveal inserts of approximately 1.3 and 1.4 kilobases, which were sub-cloned for sequence analysis. The polyadenylated RNA was hybridized with the cDNA insert and hybrid selected RNA translated in vitro. The translation products and proteins were examined by SDS-PAGE. The 1.4 kilobase insert was used to generate unidirectional deletion clones which were, in turn, used for sequencing.

Sequencing of the serpin cDNA revealed a sequence identity of the deduced amino acid sequence with that of elastase inhibitor, and it is believed, therefore, that the *M. sexta* serpin is elastase specific. Additionally, alignment of the *M. sexta* alaserpin protein sequence with other members of the serpin superfamily reveals between 15 and 30% homology.

The following examples are provided by way of illustration of the invention and are specifically directed to the procedures carried out in the isolation and purification of the *M. sexta* serine proteinase inhibitor, to procedures resulting in the identification, to procedures resulting in the sequencing and characterization of the cDNA clone, and to procedures resulting in determination of activity.

More particularly, Example 1 is directed to isolation of a fat body cDNA clone and hybrid select translation. Example 2 is directed to nucleotide and amino acid sequencing. Example 3 is directed to characterization of the *M. sexta* cDNA. Example 4 is directed to studying the activity and specificity of the serpin.

EXAMPLE 1

A. Isolation, cDNA Library Construction and Screening

*M. sexta* eggs were obtained and larvae were reared from the eggs. Total RNA was isolated from the fat body of day 2 fifth instar male larvae and polyadenylated RNA was selected by passing twice through an oligo(dT)-cellulose column. 5 µg of polyadenylated RNA was used to prepare cDNA using a commercial kit (Amersham Corp.). A cDNA library was constructed in λgt11 and screened with antiserum to *M. sexta* apolipophorin-II. (See, e.g., Shapiro, J. P., et al, *J. Biol. Chem.*, 259, pp. 3680–3685 (1984). Analysis of 12,000 recombinant plaques yielded two positive clones which were purified to homogeneity. Digestion of these two clones with EcoRl revealed inserts of approximately 1.3 and 1.4 kb. The 1.4 kb insert was subcloned into pUC8 and then into M13-mp18 for sequence analysis. RNA was fractionated in formaldehyde gels and transferred to nitrocellulose. Hybridizations with the cDNA insert labeled with $^{32}P$ by nick translation were performed.

B. Hybrid Select Translation

Hybrid selection was then carried out. 5 µg of plasmid DNA containing the 1.4 kb insert was linearized with EcoRI and spotted onto a dry 1-cm² nitrocellulose filter. The DNA was denatured in 0.5N NaOH, 1.5M NaCl, neutralized in 2M Tris pH 7.4, and 2×SSC and baked for 2 hours at 80° C. under vacuum. The filter was incubated for 30 min. at 42° C. in hybridization buffer (50% formamide, 750 mM NaCl, 40 mM Pipes, pH 6.4, 0.2% SDS and 5 mM EDTA) and then in 30 µl of hybridization buffer containing 150 µg/ml of polyadenylated RNA for 4 hours at 42° C. The filter was then washed twice with 1 ml of hybridization buffer at 42° C.; once with 1 ml of the wash buffer (150 mM NaCl, 40 mM Pipes, pH 6.4, 0.2% SDS and 5 mM EDTA) at 42° C., eight times with 1 ml of the wash buffer at 60° C. and twice with 1 ml of 2 mM EDTA at 60° C. The hybridized RNA was eluted by boiling the filter for 1 min. in 200 µl of 1 mM EDTA, pH 7.9, containing 5 µg of tRNA and quick freezing in a dry ice/ethanol bath. The solution was allowed to thaw on ice, and RNA was then precipitated with ethanol and dissolved in 10 µl of water. The RNA was translated in vitro using rabbit reticulocyte lysate (Promega) and [$^{35}S$]methionine as described in the protocol supplied with the kit. Total translation products and immunoprecipitated proteins were examined by SDS-PAGE carried out in a 10% acrylamide gel and subjected to fluorography.

EXAMPLE 2

The 1.4 kb EcoRl insert subcloned into M13-mp18 in both orientations was used to generate unidirectional deletion clones by exonuclease III. (See, e.g., Henikoff, S., *Gene* (Amst.), 28, 351–359, (1984). Single stranded DNA was sequenced by the dideoxy chain termination method. (See, e.g., Sanger, F., et al, *Proc. Natl. Acad. Aci. U.S.A.*, 74, pp. 5463–5467 (1977).

EXAMPLE 3

The National Biomedical Research Foundation protein sequence data base was searched with the FASTP program, and the significance of similarity of the sequences was determined with the RDF program. (See, Lipman, D. J., et al, *Science*, 227, pp. 1435–1441 (1985). Progressive sequence alignment and construction of phylogenetic trees were performed with the computer programs of Feng and Doolittle (See, Feng, D. F., and Doolittle, D. F., *J. Mol. Evol.*, 25, pp. 351–360 (1987). Serpin sequences were obtained from human $\alpha_1$-antitrypsin, antithrombin, chicken ovalbumin, gene-Y ovalbumin-related protein, $\alpha_2$-antiplasmin, rat angiotensinogen, $\alpha_1$-antichymotrypsin, human glia-derived nexin, endothelial cell-type plasminogen activator inhibitor, protein C inhibitor and cowpox virus hemorrhage-specific protein.

EXAMPLE 4

A. Purification of a Hemolymph Elastase Inhibitor

Hemolymph from day 3 fifth instar larvae (20 ml) was collected into 5 ml of cold 0.1M sodium phosphate, pH 7.0, 10 mM glutathione, 1 mM diisopropyl fluorophosphate. Hemocytes were removed by centrifugation, and the supernatant was dialyzed against 20 mM ammonium acetate, pH 6.0. A precipitate was removed by centrifugation (5000×g, 10 min.), and the supernatant was applied to a column of DEAE-Bio-Gel (1×20 cm) equilibrated with 20 mM ammonium acetate, pH 6.0. The column was eluted with 100 ml of the starting buffer and then with a gradient of 0–200 mM NaCl in starting buffer (300 ml total). Five-ml fractions were collected at 1 ml/min. Proteinase inhibitor activity was assayed by mixing 10 µl samples from column fractions with 1 µg porcine pancreatic elastase and residual activity assayed by placing the reaction mixture in a well cut into an agarose gel containing casein (protease substrate gel tablets, Bio-Rad). After 16 hours clear circles around the wells were measured, and protease activity was expressed as the area of the gel in which casein was hydrolyzed. For calculations of total activity, 1 unit was defined as the amount of sample required to give 50% inhibition of 1 µg of elastase. Fractions 57–59, which contained elastase inhibitory activity, were pooled and applied to a column of Sephacryl S-200 (90×1 cm), which was eluted with 20 mM ammonium acetate, pH 6.7. Five-ml fractions were collected at 0.3 ml/min. Fractions were assayed for anti-elastase activity as described above. Fractions 20–23, corresponding to a peak of elastase inhibitory activity, were pooled.

B. Analysis of Manduca Elastase Inhibitor

Steps during the purification were analyzed for antielastase and the molecular weight of the hemolymph elastase inhibitor was determined by SDS-PAGE carried out in a 5–15% acrylamide gradient gel and stained with Coomassie Blue. The NH$_2$-terminal amino acid sequence was determined. The carbohydrate content was determined by the phenol/sulfuric acid method. Protein-bound carbohydrate was further analyzed by staining SDS-polyacrylamide gels with fluorescein isothiocyanate-conjugated concanavalin A (Sigma). The isoelectric point of the protein was estimated by isoelectric focusing in a pH 3–9 gel (Phast System, Pharmacia LKB Biotechnology, Inc.). Antiserum was produced in New Zealand White rabbits by intramuscular injection of 100 μg by intramuscular injection of 100 μg of elastase inhibitor in Freund's complete adjuvant followed after six weeks by injection of 100 μg of elastase inhibitor in Freund's incomplete adjuvant. Blood was collected after two weeks, and serum was stored at −70° C. The antiserum was characterized by Western blot analysis of hemolymph proteins and found to be specific for the 47,000 dalton elastase inhibitor.

Association constants for the purified hemolymph proteinase inhibitor and various serine proteinases were determined under second order conditions. Bovine trypsin and chymotrypsin and porcine pancreatic elastase were obtained from Sigma. After allowing equimolar concentrations of enzyme and inhibitor to react for various periods of time, residual enzyme activity was measured at 25° C. in 0.1 mM Tris-HCl, pH 8.0, using 0.5 mM N-succinyl-L-alanyl-L-alanyl-L-prolyl-L-leucyl-p-nitroanalide (Sigma) as a substrate for elastase, 0.1 mM N-succinyl-L-alanyl-L-alanyl-L-prolyl-L-phenylalanyl-p-nitroanalide as a substrate for chymotrypsin, and 0.5 mM N-benzoyl-L-arginyl-ethyl ester (Sigma) as a substrate for trypsin.

It should be readily apparent from the foregoing illustrative examples that numerous potential products are provided by the present invention. The polypeptide provided by this invention may be useful in various expression systems and products or in synthetic products, the structure of which was first made known by the present invention.

Turning now to the accompanying figures, the results of the foregoing examples are shown. After screening the *M. sexta* fat body cDNA library with antiserum thought to be specific for apolipophorin-II, as described in Example 1, two clones were isolated that hybridized to a fat body RNA of 1470 nucleotides. This fat body RNA was too small to encode apolipophorin-II (M$_r$=78,000). The clone containing the 1.4 kb insert was used to identify a protein product of the corresponding mRNA by hybrid select translation. FIG. 1 illustrates the SDS-PAGE staining pattern of the total translation products (lane 3), the RNA translation products selected by hybridization with alaserpin cDNA (lane 4) and immunoprecipitated translation products of hybrid select RNA (lane 5); all having a M$_r$ equal to about 46,000 daltons.

Figure 2:
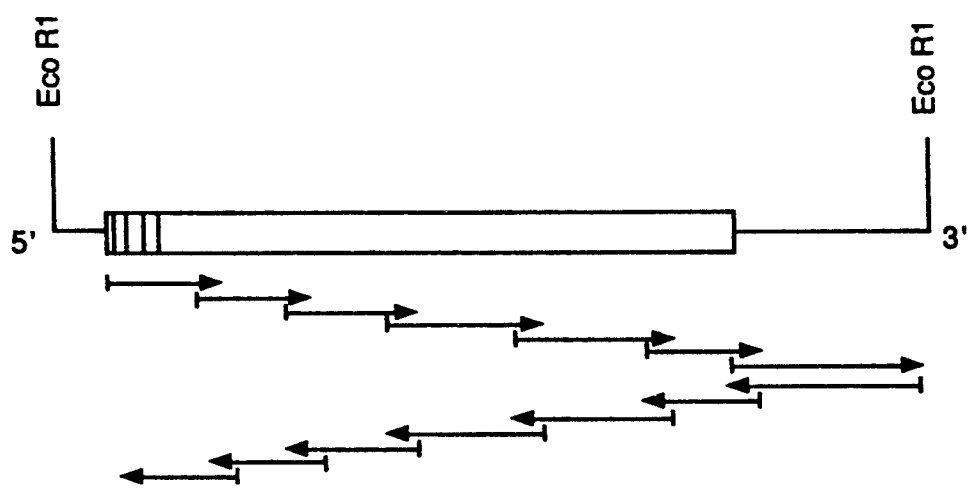
FIG. 2 is a diagrammatic representation of the sequencing strategy for *M. sexta* alaserpin cDNA.

To learn more about this 46,000 dalton protein, the 1.4 kb cDNA clone was sequenced as described in Example 2. The strategy for sequencing is shown in FIG. 2 and the nucleotide and deduced amino acid sequence is shown in FIG. 3. In FIG. 2 the box indicates the sequence coding for the protein and the shaded area adjacent to the 5' end indicates the sequence coding for the signal peptide. Arrows indicate the direction and extent of each sequence determination. In FIG. 3 the amino acids in the mature hemolymph protein are assigned positive numbers, those in the putative signal peptide are assigned negative numbers.

Amino acids which are underlined were confirmed by protein sequencing. The 1427-base pair cDNA sequence contains an open reading frame beginning with an ATG codon at position 25 and the translated DNA extends to position 1200, followed by a 227 base pair 3'-untranslated sequence. The above open reading frame from position 25 to position 1200 codes for the serine proteinase inhibitor. While this clone does not contain a poly(A) tail, a consensus polyadenylation signal, AATAAA, is present beginning at position 1414. The 5 nucleotides upstream from the ATG codon are GCAAC, which match in three positions with a consensus sequence for eukaryotic initiation sites, including the highly conserved purine at position-3.

As described in Example 3, sequence alignment of the *M. sexta* protein with other members of the serpin superfamily of proteinase inhibitors demonstrated sequence similarities ranging from about 31.7% identical residues when compared with human plasminogen activator inhibitor, to about 15.8% identity with rat angiotensinogen. Identical residues appear throughout the sequences, with greater similarity in the COOH-terminal halves of the proteins. The same amino acid is present in fifteen positions in all sequences and another 41 positions with identical amino acids in at least nine of the twelve proteins. These data support the conclusion that the *M. sexta* cDNA codes for a member of the serpin superfamily.

The sequence alignments also permit a prediction of the location of the reactive center of the *M. sexta* protein. The P$_1$ residue of the reactive center, which determines inhibitor specificity, is predicted to be alanine at position 343 of the mature protein. According to the serpin classifications of Carrell, R., et al, *Trends Biochem. Sci.*, 10, pp. 20–24 (1985), which classifies serpins according to their reactive center, the *M. sexta* protein is an alaserpin, and its specificity should be toward proteinases, such as elastase, which cleave at alanine. Table 1, modified from Carrell, et al, presents a comparison of the predicted reactive center of the *M. sexta* serpin with those of known vertebrate serpins.

TABLE I

| Inhibitor | Target | Reactive center residues | | | | | |
|---|---|---|---|---|---|---|---|
| | | P$_2$ | P$_1$ | P$_1$' | P$_2$' | P$_3$' | P$_4$' |
| α$_1$-Antitrypsin | Elastase | Pro | Met | Ser | Ile | Pro | Pro |
| α$_1$-Antichymotrypsin | Chymase | Leu | Leu | Ser | Ala | Leu | Val |
| Antithrombin-III | Thrombin | Gly | Arg | Ser | Leu | Asn | Pro |
| Mouse contrapsin | "Trypsin" | Arg | Lys | Ala | Ile | Leu | Pro |
| Ovalbumin | ?Elastase | Ala | Ala | Ser | Val | Ser | Glu |
| *M. sexta* alaserpin | ?Elastase | Pro | Ala | Ser | Leu | Ile | Leu |

Figure 4:
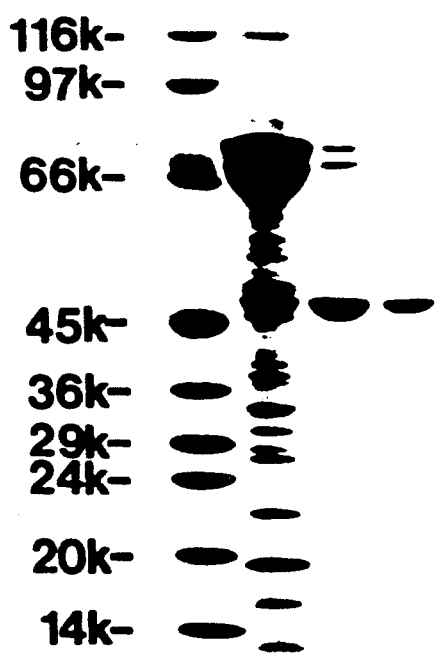
FIG. 4 is a SDS-PAGE staining pattern of *M. sexta* alaserpin at different stages of purification. Lane 1 represents protein standards; lane 2 represents hemolymph from day 3 fifth instar *M. sexta* larvae; lane 3 represents alaserpin after ion-exchange chromatography; and lane 4 represents alaserpin after gel filtration.

Having determined the predicted size, amino acid composition, and proteinase specificity of the *M. sexta* alaserpin, isolation and purification of the hemolymph elastase inhibitor was conducted. Example 4 describes the isolation and purification procedures, FIG. 4 shows SDS-PAGE staining patterns of *M. sexta* alaserpin at different stages of purification, wherein lane 2 corresponds to the hemolymph from day 3 fifth instar larvae and shows numerous protein bands with broad staining bands centered around 66 and 46 kDa, lane 3 represents the hemolymph elastase inhibitor after ion-exchange chromatography on DEAE-Bio-Gel which separated the elastase inhibitor from the majority of other hemolymph proteins, and lane 4 represents the elastase inhibitor after gel filtration on Sephacryl S-200. Table II summarizes the results of the isolation procedure.

TABLE II

| Step | Total Volume ml | Total Activity units | Total Protein mg | Specific Activity units/mg | Yield % | Purification -fold |
|---|---|---|---|---|---|---|
| 1. Hemolymph | 20 | 28,000 | 340 | 82 | | |
| 2. DEAE | 15 | 24,000 | 5.6 | 4,286 | 86 | 52 |
| 3. Sephacryl | 18 | 6,920 | 1.17 | 5,915 | 25 | 72 |

Finally, elastase specificity of the *M. sexta* alaserpin was determined by measuring the association rate constants ($k_{assoc}$) for the inhibitor with porcine pancreatic elastase, bovine chymotrypsin and bovine trypsin. The *M. sexta* alaserpin had a $k_{assoc}$ of $1 \times 10^7$ $M^{-1} s^{-1}$ for elastase, $7 \times 10^4$ $M^{-1} s^{-1}$ for chymotrypsin, and $5 \times 10^2$ $M^{-1} s^{-1}$ for trypsin. These results were consistent with the predicated specificity from the sequence at the active center of the inhibitor.

Thus, the present invention presents, for the first time, the isolated and characterized cDNA and protein for a serin proteinase inhibitor which is a member of the serpin superfamily from the insect *M. sexta*. The gene is expressed in the fat body and the protein is secreted into the hemolymph. The purified *M. sexta* serpin has been determined to be specific for elastase.

The extent to which the DNA sequence of the present invention will have use in various alternative methods of protein synthesis or expression systems in transgenic insects or other species cannot yet be determined. Viewed in this light, therefore, the specific disclosures of the illustrative examples are not intended to be limiting upon the scope of the present invention and numerous modifications and variations are expected to occur to those skilled in the art. As one example, while the DNA sequence provided by the examples includes cDNA and genomic DNA sequences, because this application provides amino acid sequence information essential to manufacture of DNA sequences, the invention also comprehends such manufactured DNA sequences as may be constructed based upon knowledge of the DNA sequences of the serpin superfamily. These may code for the *M. sexta* alaserpin, as well as for fragments thereof and serpin analogs which may share one or more biological properties of naturally-occurring serine proteinase inhibitors, but not share others.

The DNA sequence provided by the present invention is, therefore seen, to comprehend all DNA sequences suitable for use in securing procaryotic or eucaryotic expression of a polypeptide product having at least a part of the primary structural conformation and one or more of the biological properties of *M. sexta* alaserpin.

What is claimed is:

1. A purified DNA molecule having a sequence defined by nucleotides 25–1200 of FIG. 3 which encodes for Manduca sexta hemolymph serine proteinase inhibitor.

2. The purified DNA sequence of claim 1 further including a 5'-untranslated eukaryotic initiation site and a 3'-untranslated eukaryotic polyadenylation signal, said eukaryotic initiation site consisting essentially of the nucleotide sequence CGAAC appearing at nucleotide positions 20–24 of FIG. 3 and said polyadenylation signal consisting essentially of the nucleotide sequence AATAAA appearing at nucleotide positions 1414–1419 of FIG. 3.

3. A purified DNA sequence complementary to the sequence of claim 1.

4. An isolated and purified DNA molecule encoding the amino acid sequence for *Manduca sexta* hemolymph serine proteinase inhibitor as set forth in FIG. 3.

* * * * *